(12) United States Patent  (10) Patent No.: US 8,146,589 B2
Djupesland  (45) Date of Patent: Apr. 3, 2012

(54) NASAL DEVICES

(75) Inventor: Per Gisle Djupesland, Oslo (NO)

(73) Assignee: OptiNose AS, Oslo (NO)

( * ) Notice: Subject to any disclaimer, the term of this patent is extended or adjusted under 35 U.S.C. 154(b) by 617 days.

(21) Appl. No.: 10/509,552

(22) PCT Filed: Mar. 28, 2003

(86) PCT No.: PCT/IB03/01557
§ 371 (c)(1),
(2), (4) Date: Jun. 9, 2005

(87) PCT Pub. No.: WO03/082393
PCT Pub. Date: Oct. 9, 2003

(65) Prior Publication Data
US 2005/0235992 A1  Oct. 27, 2005

(30) Foreign Application Priority Data
Mar. 28, 2002 (GB) .................................. 0207422.7

(51) Int. Cl.
*A61M 15/00* (2006.01)
(52) U.S. Cl. ......... 128/203.18; 128/203.12; 128/203.15; 128/207.18; 128/203.22; 128/203.25
(58) Field of Classification Search ............ 128/201.13, 128/203.12, 203.14, 203.15, 203.18, 203.19, 128/203.22, 203.23, 203.25, 203.24, 203.29, 128/204.18, 204.21, 204.26, 205.24, 205.25, 913
See application file for complete search history.

(56) References Cited

U.S. PATENT DOCUMENTS

| | | | |
|---|---|---|---|
| 2,566,806 A | 9/1951 | Miller | |
| 4,407,279 A | 10/1983 | Tschernezky | |
| 5,046,491 A * | 9/1991 | Derrick ................. | 128/200.24 |
| 5,099,836 A | 3/1992 | Loescher et al. | |
| 5,271,391 A | 12/1993 | Graves | |
| 5,392,772 A | 2/1995 | Zilbershtein | |
| 6,019,100 A * | 2/2000 | Alving et al. ........... | 128/203.12 |
| 6,142,147 A | 11/2000 | Head et al. | |
| 6,715,485 B1 * | 4/2004 | Djupesland ............. | 128/203.15 |
| 7,377,901 B2 | 5/2008 | Djupesland et al. | |
| 2004/0112378 A1 | 6/2004 | Djupesland | |
| 2004/0112379 A1 | 6/2004 | Djupesland | |

(Continued)

FOREIGN PATENT DOCUMENTS
GB  408856  4/1934
(Continued)

*Primary Examiner* — Clinton T Ostrup
(74) *Attorney, Agent, or Firm* — Proskauer Rose LLP

(57) ABSTRACT

A nasal delivery device (11) for delivering substance to a nasal airway (1) of a subject, comprising: first and second nosepiece units (17, 19), each including a nosepiece (21, 23) for fitting to respective nostrils of a subject; at least one substance supply unit (13, 15) for supplying substance for delivery to the nasal airway (1) of the subject; and a valve unit (35, 37) for selectively fluidly connecting the at least one substance supply unit (13, 15) alternately to respective ones of the nosepiece units (17, 19).

34 Claims, 13 Drawing Sheets

U.S. PATENT DOCUMENTS

| | | |
|---|---|---|
| 2004/0149289 A1 | 8/2004 | Djupesland |
| 2004/0182388 A1 | 9/2004 | Djupesland |
| 2005/0028812 A1 | 2/2005 | Djupesland |
| 2005/0072430 A1 | 4/2005 | Djupesland |
| 2005/0235992 A1 | 10/2005 | Djupesland |
| 2006/0096589 A1 | 5/2006 | Djupesland |
| 2006/0107957 A1* | 5/2006 | Djupesland ............ 128/206.11 |
| 2006/0219240 A1 | 10/2006 | Djupesland |
| 2006/0219241 A1 | 10/2006 | Djupesland |
| 2006/0225732 A1 | 10/2006 | Djupesland |
| 2006/0231094 A1 | 10/2006 | Djupesland |
| 2007/0039614 A1 | 2/2007 | Djupesland |
| 2007/0125371 A1 | 6/2007 | Djupesland |
| 2008/0161771 A1 | 7/2008 | Djupesland |

FOREIGN PATENT DOCUMENTS

| | | |
|---|---|---|
| WO | WO 92/011054 | 7/1992 |
| WO | 98/53869 | 12/1998 |
| WO | 99/19013 | 4/1999 |
| WO | 00/51672 | 9/2000 |
| WO | WO 00/064521 | 11/2000 |
| WO | 01/78818 | 10/2001 |
| WO | WO 0197689 A1 * | 12/2001 |
| WO | WO 02068029 A2 * | 9/2002 |

* cited by examiner

NASAL DEVICES

This application is a national phase of International Application No. PCT/IB03/01557 filed Mar. 28, 2003 and published in the English language.

The present invention relates to a nasal delivery device for and a method of delivering substance, in particular one of a liquid, as a suspension or solution, or a powder containing a medicament, especially systemic or topical pharmaceuticals, or a vaccine to the nasal airway of a subject.

Referring to FIG. 1, the nasal airway 1 comprises the two nasal cavities 2, 3 separated by the nasal septum 4, which airway 1 includes numerous ostia, such as the paranasal sinus ostia 5 connected to the paranasal sinuses 6 and the tubal ostia 7 connected to the tuba auditiva 8 and the middle ears 9, and olfactory cells, and is lined by the nasal mucosa. The nasal airway 1 can communicate with the nasopharynx, the oral cavity and the lower airway, with the nasal airway 1 being in selective communication with the anterior region of the nasopharynx and the oral cavity by opening and closing of the oropharyngeal velum.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and antibiotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitionin, and analgetics, such as anti-migraine compositions, as the high blood flow and large surface area of the nasal mucosa advantageously provides for rapid systemic uptake.

Nasal delivery is also expected to be advantageous for the administration of medicaments requiring a rapid onset of action, for example, analgetics, anti-emetics, insulin, anti-epileptics, sedatives and hypnotica, and also other pharmaceuticals, for example, cardio-vascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

It is also expected that nasal delivery could provide an effective delivery route for the administration of proteins and peptides as produced by modern biotechnological techniques. For such substances, the metabolism in the intestines and the first-pass-effect in the liver represent significant obstacles for reliable and cost-efficient delivery.

Furthermore, it is expected that nasal delivery using the nasal delivery technique of the present invention will prove effective in the treatment of many common neurological diseases, such as Alzheimer's, Parkinson's, psychiatric diseases and intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Also, it is expected that the nasal delivery technique of the present invention will allow for the effective delivery of vaccines.

Aside from the delivery of medicaments and vaccines, the irrigation of the nasal mucosa with liquids, in particular saline solutions, is commonly practised to remove particles and secretions, as well as to improve the mucociliary activity of the nasal mucosa. These solutions can be used in combination with active pharmaceuticals.

For any kind of drug delivery, accurate and reliable dosing is essential, but it is of particular importance in relation to the administration of potent drugs which have a narrow therapeutic window, drugs with potentially serious adverse effects and drugs for the treatment of serious and life-threatening conditions. For some conditions, it is essential to individualize the dosage to the particular situation, for example, in the case of diabetes mellitus. For diabetes, and, indeed, for many other conditions, the dosage of the pharmaceutical is preferably based on actual real-time measurements. Currently, blood samples are most frequently used, but the analysis of molecules in the exhalation breath of subjects has been proposed as an alternative to blood analysis for several conditions. Breath analysis is currently used for the diagnosis of conditions such as *helicobacter pylori* infections which cause gastric ulcers.

WO-A-00/51672 discloses a delivery device for delivering substance, in particular a medicament, in a bi-directional flow through the nasal cavities, that is, an air flow which passes into one nostril, around the posterior margin of the nasal septum and in the opposite direction out of the other nostril. This bi-directional air flow advantageously acts to stimulate the sensory nerves in the nasal mucosa, thereby conditioning the subject for the delivery and providing a more comfortable delivery situation.

It is an aim of the present invention to provide an improved nasal delivery device for and method of delivering substance to the nasal airway of a subject.

In one aspect the present invention provides a nasal delivery device for delivering substance to a nasal airway of a subject, comprising: first and second nosepiece units, each including a nosepiece for fitting to respective nostrils of a subject; at least one substance supply unit for supplying substance for delivery to the nasal airway of the subject; and a valve unit for selectively fluidly connecting the at least one substance supply unit alternately to respective ones of the nosepiece units.

Preferably, the delivery device further comprises: a mouthpiece through which the subject in use exhales.

Preferably, the delivery device further comprises: a gas supply channel for supplying a gas flow for entraining substance supplied by the at least one substance supply unit.

In one embodiment the mouthpiece is fluidly connected to the gas supply channel, whereby the gas flow is an air flow developed by an exhalation breath of the subject.

In another embodiment the delivery device further comprises: a gas supply unit which is fluidly connected to the gas supply channel for delivering a gas flow through the gas supply channel.

Preferably, the gas supply unit is an exhalation breath actuatable unit which is fluidly connected to the mouthpiece such as to be actuated on exhalation by the subject.

In one embodiment the valve unit is configured alternately fluidly to connect one of the nosepiece units to the at least one substance supply unit and vent the other of the nosepiece units, such that, where the gas flow is at a driving pressure which is such as to cause the gas flow to flow around the posterior margin of the nasal septum and through the nasal airway, the gas flow delivered through the one nosepiece unit is vented through the other nosepiece unit.

Preferably, the delivery device further comprises: at least one flow resistor to which the other nosepiece unit is vented.

In one embodiment the at least one flow resistor has a fixed flow resistance for providing a fixed flow resistance to the gas flow.

In another embodiment the at least one flow resistor is a progressive resistor for progressively providing an increasing flow resistance to the gas flow.

Preferably, the progressive resistor comprises an expandable member which provides a progressively increasing resistance to the gas flow.

Preferably, the delivery device further comprises: a control unit for controlling the valve unit such as to provide for alternate delivery of substance through respective ones of the first and second nosepiece units.

In one embodiment the delivery device comprises: a single substance supply unit for supplying substance for delivery alternately to respective ones of the first and second nosepiece units.

In another embodiment the delivery device comprises: first and second substance supply units for supplying substance for delivery to respective ones of the first and second nosepiece units.

Preferably, the valve unit comprises first and second valves, each being fluidly connected to a respective one of the first and second nosepiece units.

In another aspect the present invention provides a method of delivering substance to a nasal airway of a subject, comprising the steps of: fitting first and second nosepiece units to respective nostrils of a subject; and delivering substance alternately through respective ones of the nosepiece units.

Preferably, the method further comprises the step of: exhaling through a mouthpiece during delivery of substance.

Preferably, substance is delivered in a gas flow.

In one embodiment the gas flow is an air flow developed by an exhalation breath of the subject.

In another embodiment the gas flow is a gas flow separate to an exhalation breath of the subject.

In one embodiment substance is delivered alternately through the nosepiece units and the other of the nosepiece units is vented, such that, where the gas flow is at a driving pressure which is such as to cause the gas flow to flow around the posterior margin of the nasal septum and through the nasal airway, the gas flow delivered through the one nosepiece unit is vented through the other nosepiece unit.

Preferably, the gas flow is vented through a flow resistor.

In one embodiment the flow resistor has a fixed flow resistance and provides a fixed flow resistance to the gas flow.

In another embodiment the flow resistor is a progressive resistor which provides a progressively increasing flow resistance to the gas flow.

Preferably, the progressive resistor comprises an expandable member which provides a progressively increasing resistance to the gas flow.

In one embodiment substance is supplied from a single substance supply unit.

In another embodiment substance is supplied to the first and second nosepiece units from respective ones of first and second substance supply units.

In a further aspect the present invention provides a nasal delivery device for delivering substance to a nasal airway of a subject, comprising: at least one delivery unit for delivering substance to a nasal airway of a subject; and a gas supply unit for applying a varying pressure in the nasal airway of the subject.

Preferably, the gas supply unit is configured to cycle the pressure in the nasal airway of the subject.

More preferably, the gas supply unit is configured to provide an alternating pressure in the nasal airway of the subject.

Preferably, the delivery device further comprises: a mouthpiece through which the subject in use exhales.

More preferably, the gas supply unit is an exhalation breath actuatable unit which is fluidly connected to the mouthpiece such as to be actuated on exhalation by the subject.

In yet another aspect the present invention provides a method of delivering substance to a nasal airway of a subject, comprising the steps of: delivering substance to a nasal airway of a subject; and applying a varying pressure in the nasal airway of the subject.

Preferably, the step of applying a varying pressure in the nasal airway of the subject comprises the step of: cycling the pressure in the nasal airway of the subject.

More preferably, the step of applying a varying pressure in the nasal airway of the subject comprises the step of: alternating the pressure in the nasal airway of the subject.

Preferably, the method further comprises the step of: exhaling through a mouthpiece during delivery of substance.

In a yet further aspect the present invention provides a nasal delivery device for delivering substance to a nasal airway of a subject, comprising: at least one delivery unit for delivering substance to a nasal airway of a subject; and a gas supply unit for alternately delivering and withdrawing a volume of gas through the nasal airway of the subject such as to cause entrained substance to be flushed in alternate directions therethrough.

Preferably, the delivery device further comprises: a mouthpiece through which the subject in use exhales.

In still yet another aspect the present invention provides a method of delivering substance to a nasal airway of a subject, comprising the steps of: delivering substance to a nasal airway of a subject; and alternately delivering and withdrawing a volume of gas through the nasal airway of the subject such as to cause entrained substance to be flushed in alternate directions therethrough.

Preferably, the method further comprises the step of: exhaling through a mouthpiece during delivery of substance.

In a still yet further aspect the present invention provides an interface member for attachment to a nasal delivery device, comprising, as an integral element, at least one nosepiece for fitting to a nostril of a subject and a mouthpiece through which the subject in use exhales.

Preferably, the interface member comprises first and second nosepieces for fitting to respective nostrils of a subject Preferably, the interface member is a disposable element.

In one embodiment the mouthpiece comprises a tubular section through which the subject in use exhales.

In another embodiment the mouthpiece includes a flexible member which is deflectable on exhalation into the mouthpiece.

Preferably, the mouthpiece comprises a cavity into which the subject in use exhales, with a part of the cavity being defined by the flexible member.

Preferably, the flexible member comprises a resilient member.

Preferred embodiments of the present invention will now be described hereinbelow by way of example only with reference to the accompanying drawings, in which:

FIG. 1 schematically illustrates the nasal airway of a human subject;

FIG. 2(a) schematically illustrates a nasal delivery device in accordance with a first embodiment of the present invention;

Figure 3A:
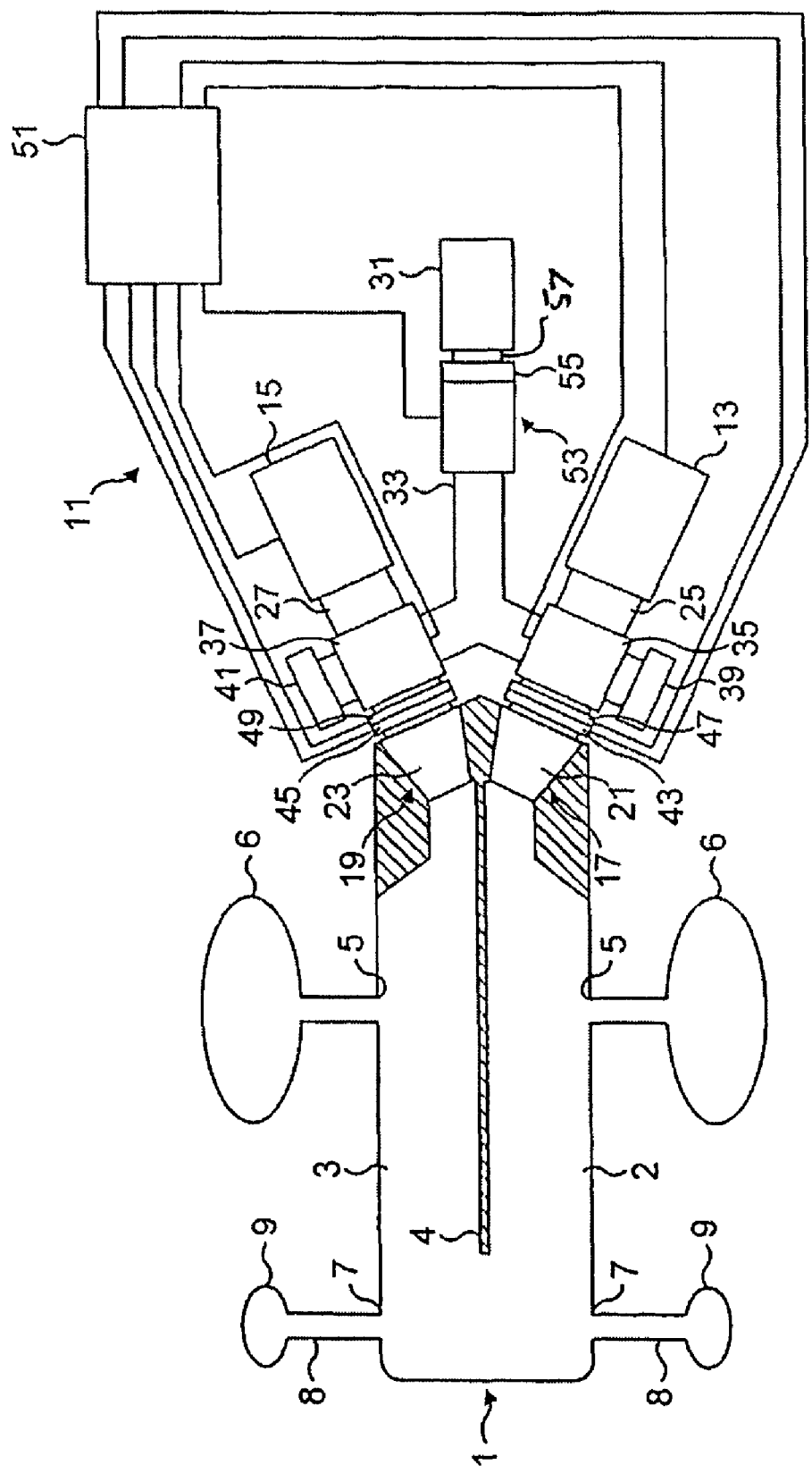
Figure 3B:
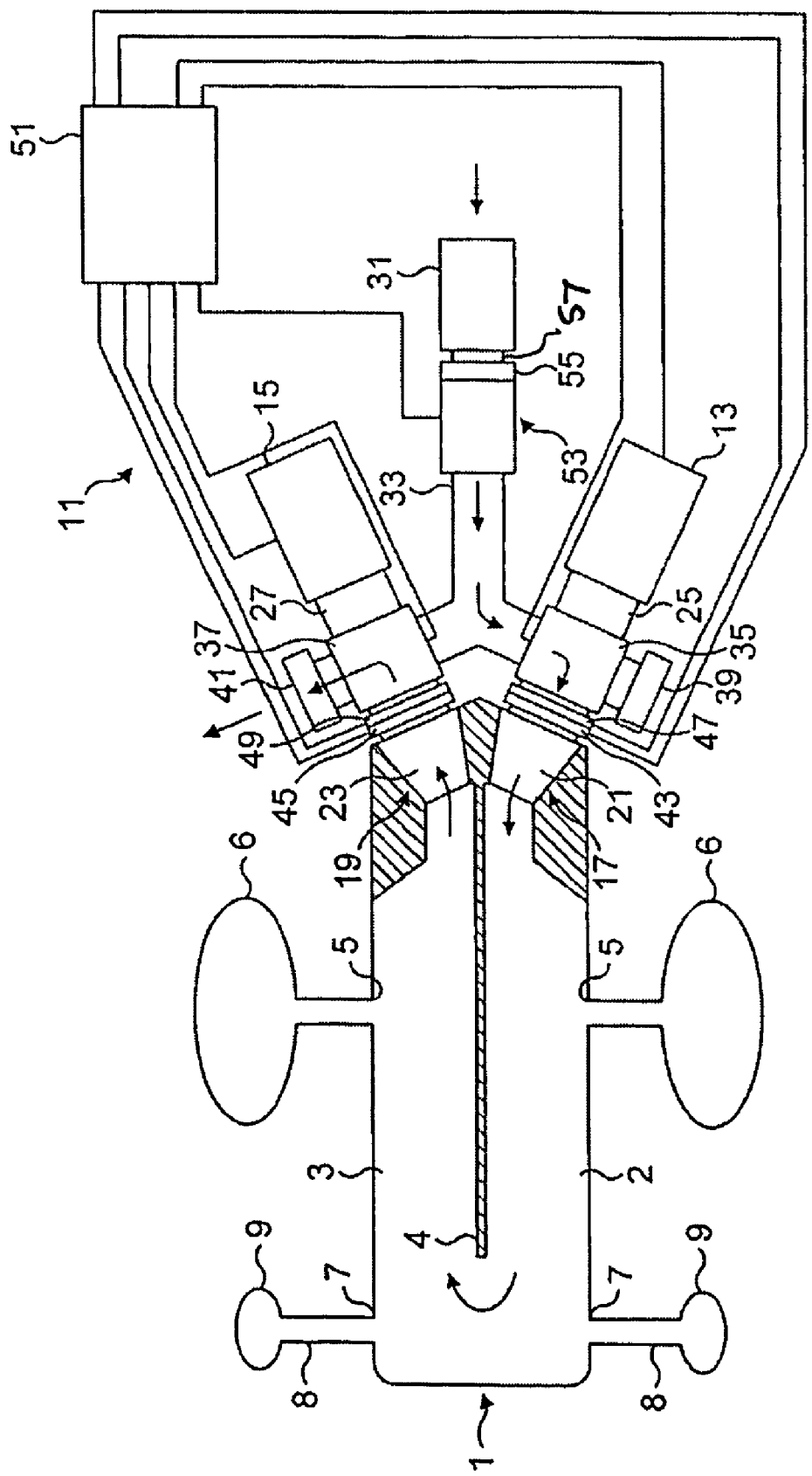
Figure 3C:
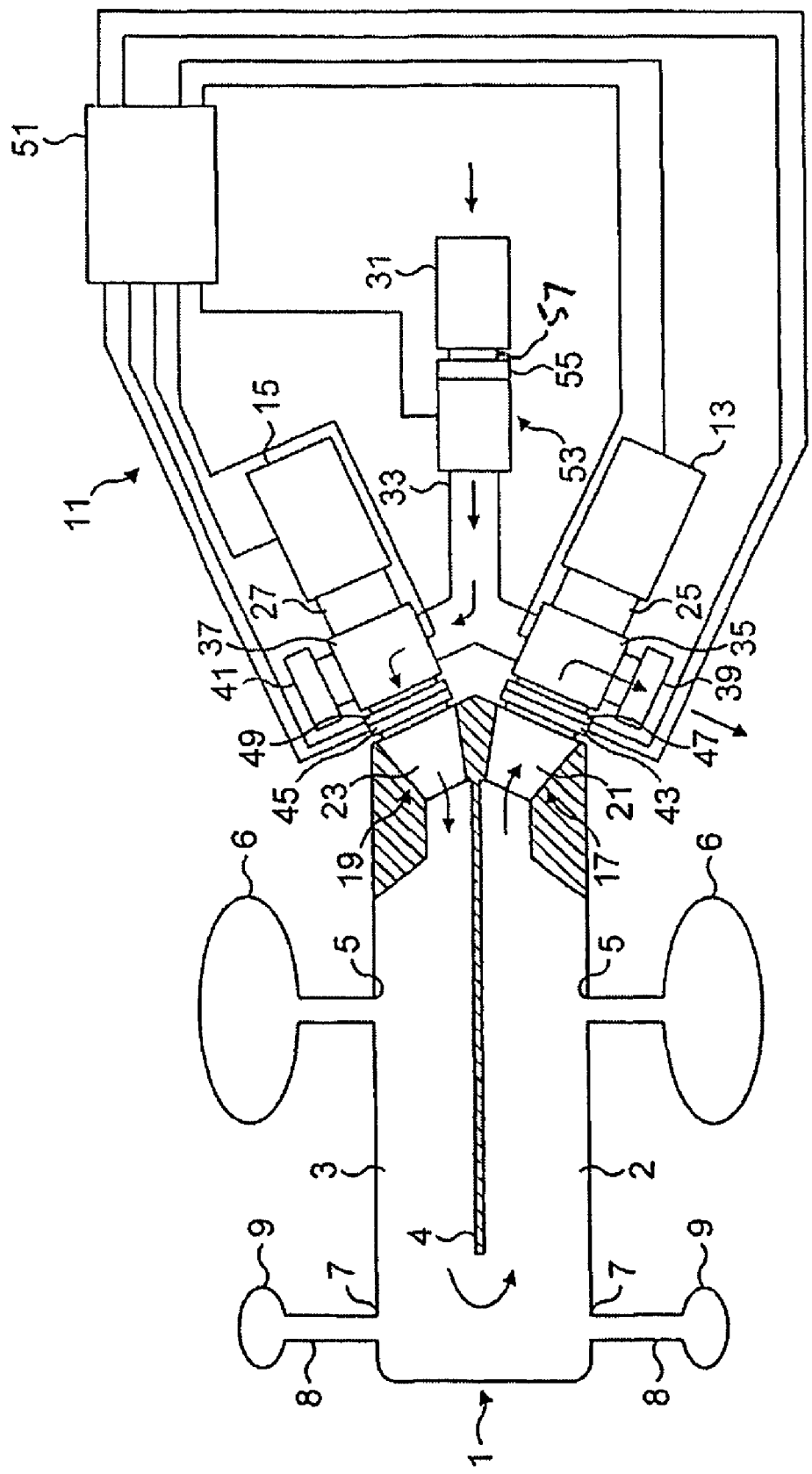
Figure 4A:
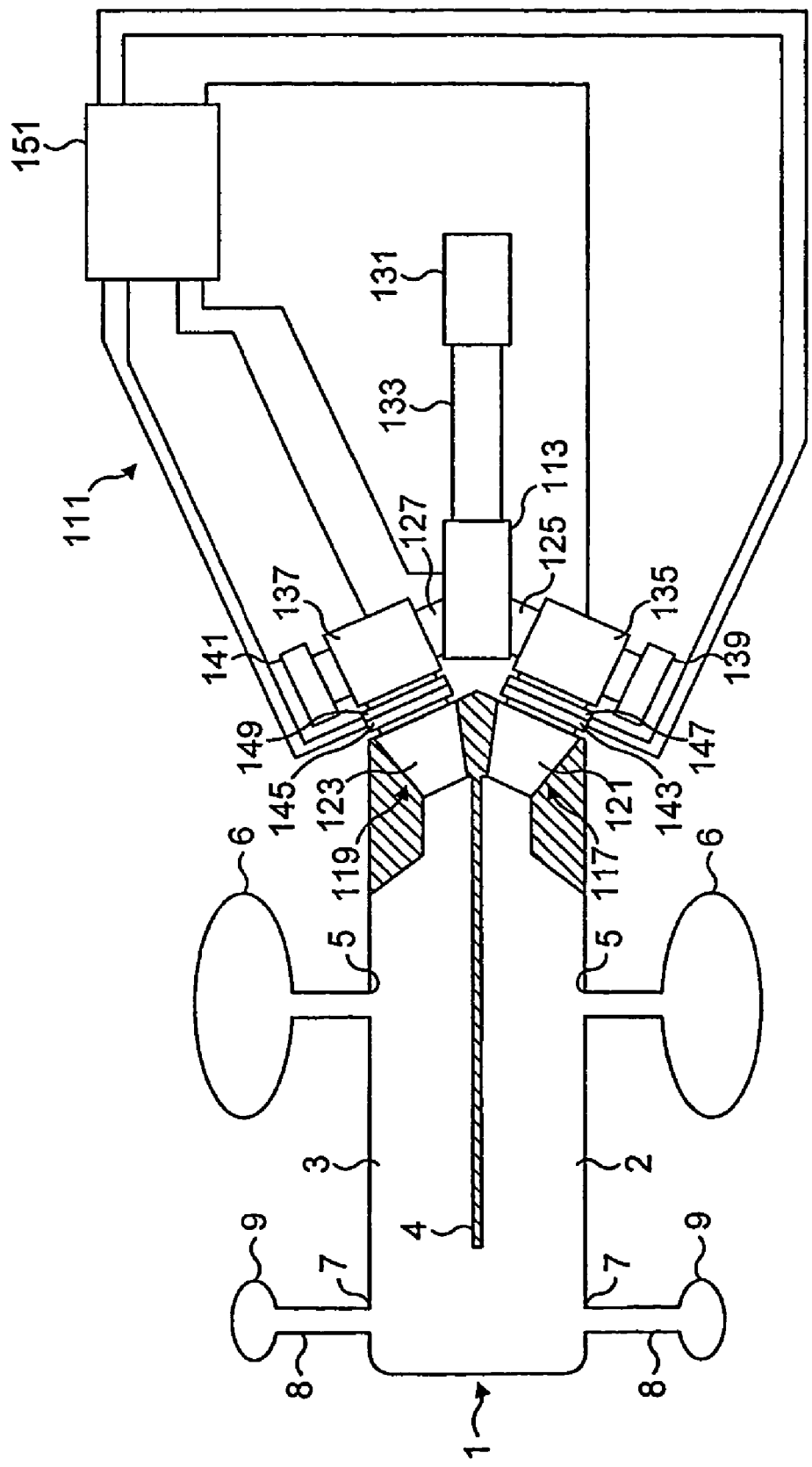
Figure 4B:
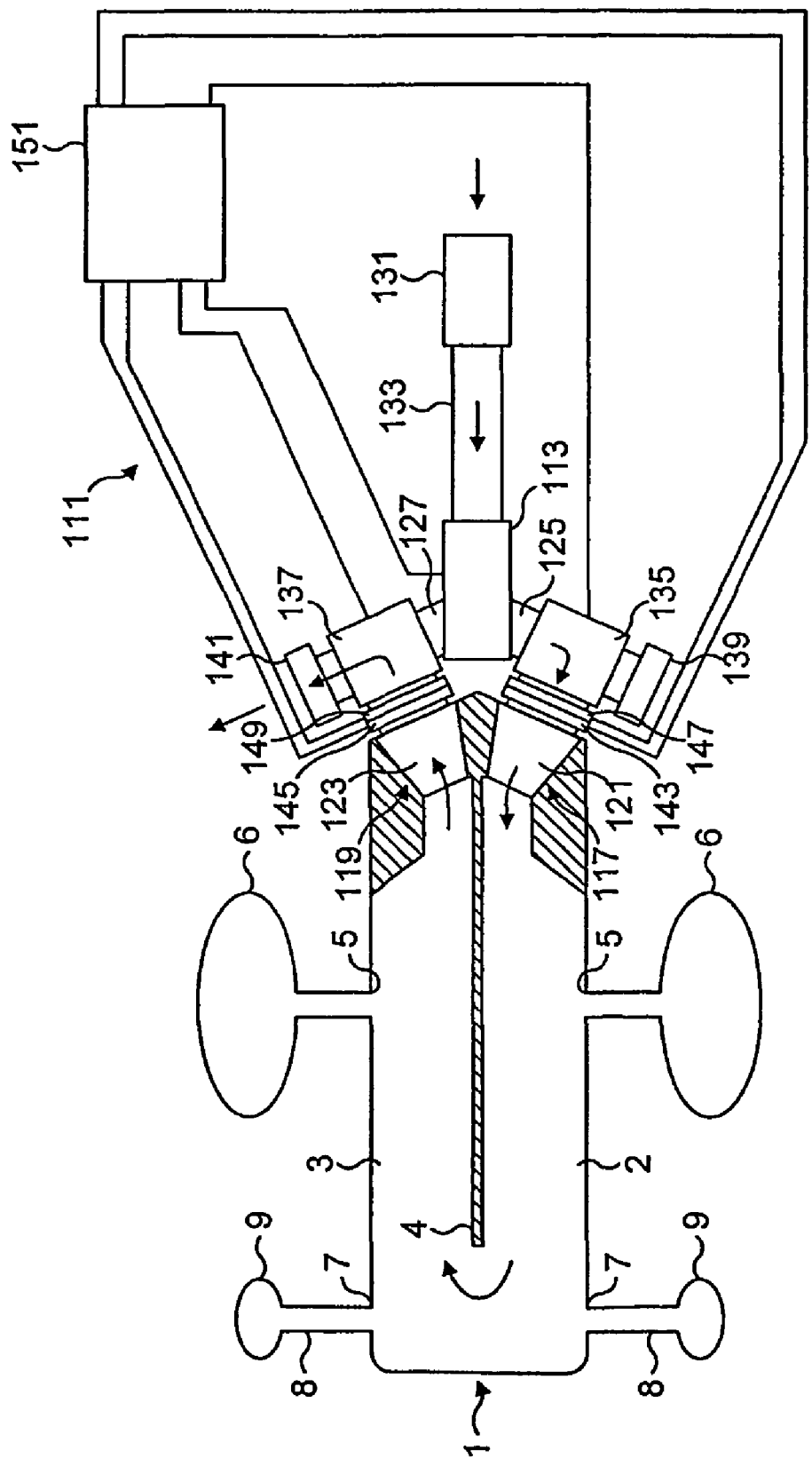
Figure 4C:
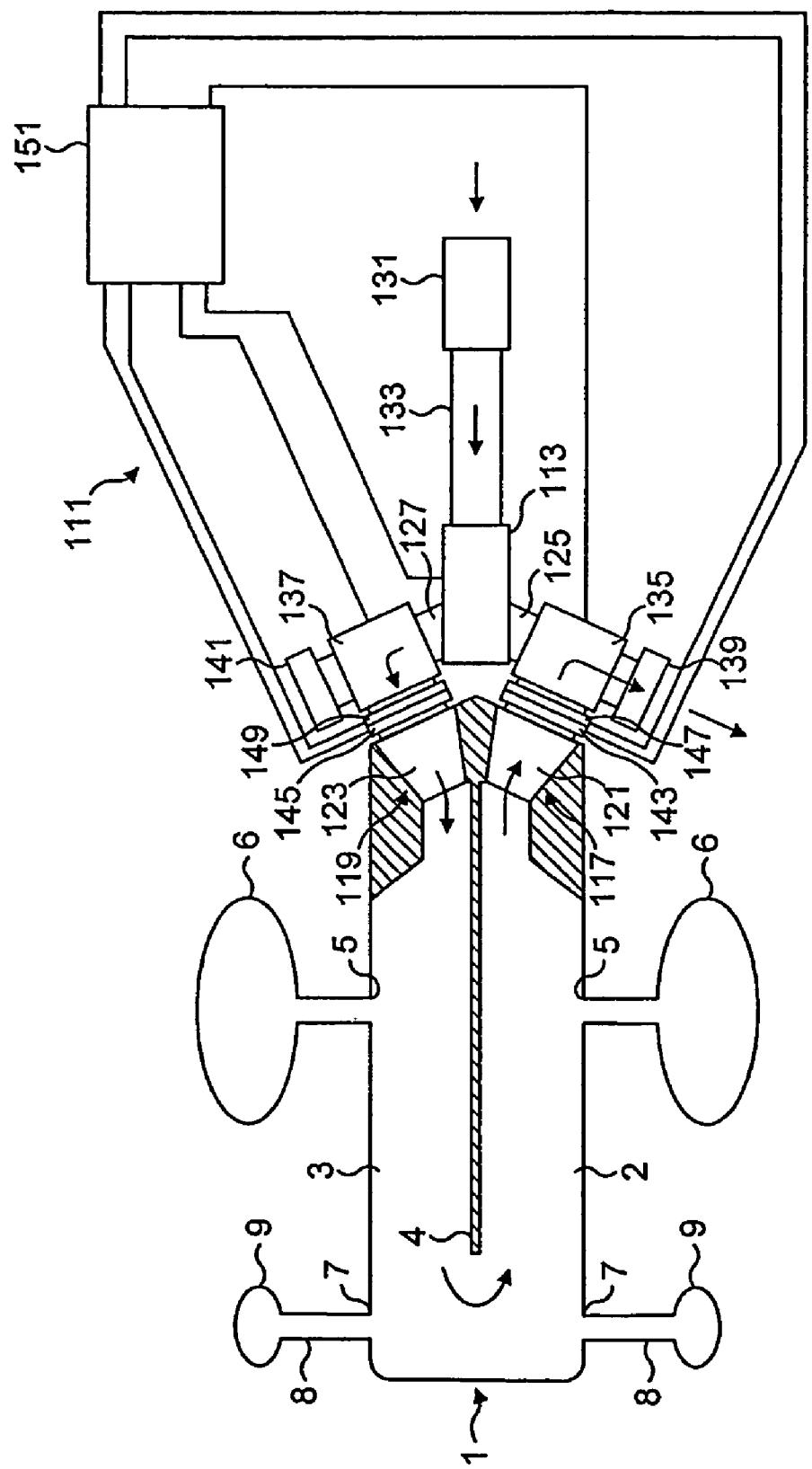
Figure 5A:
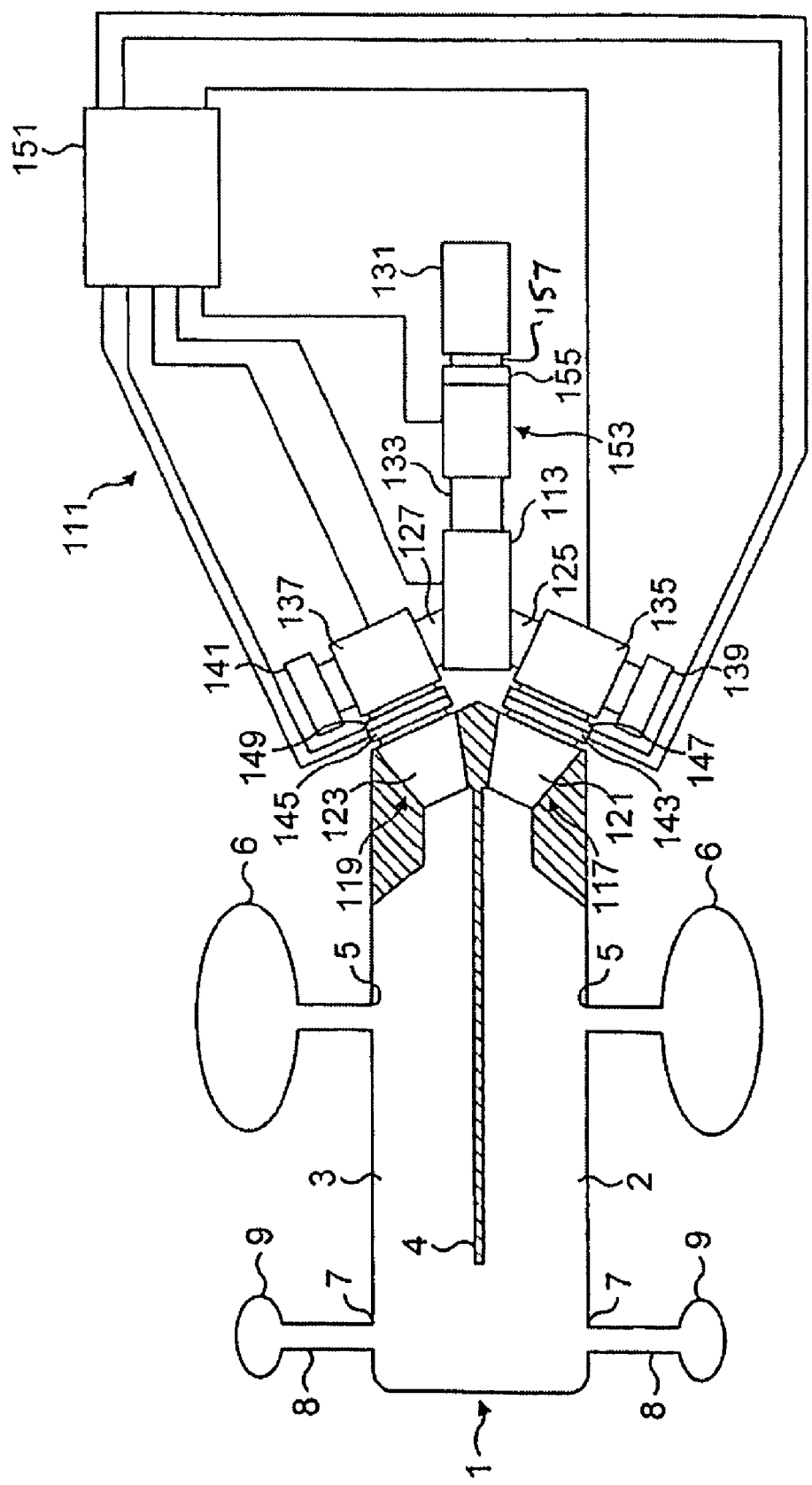
Figure 5B:
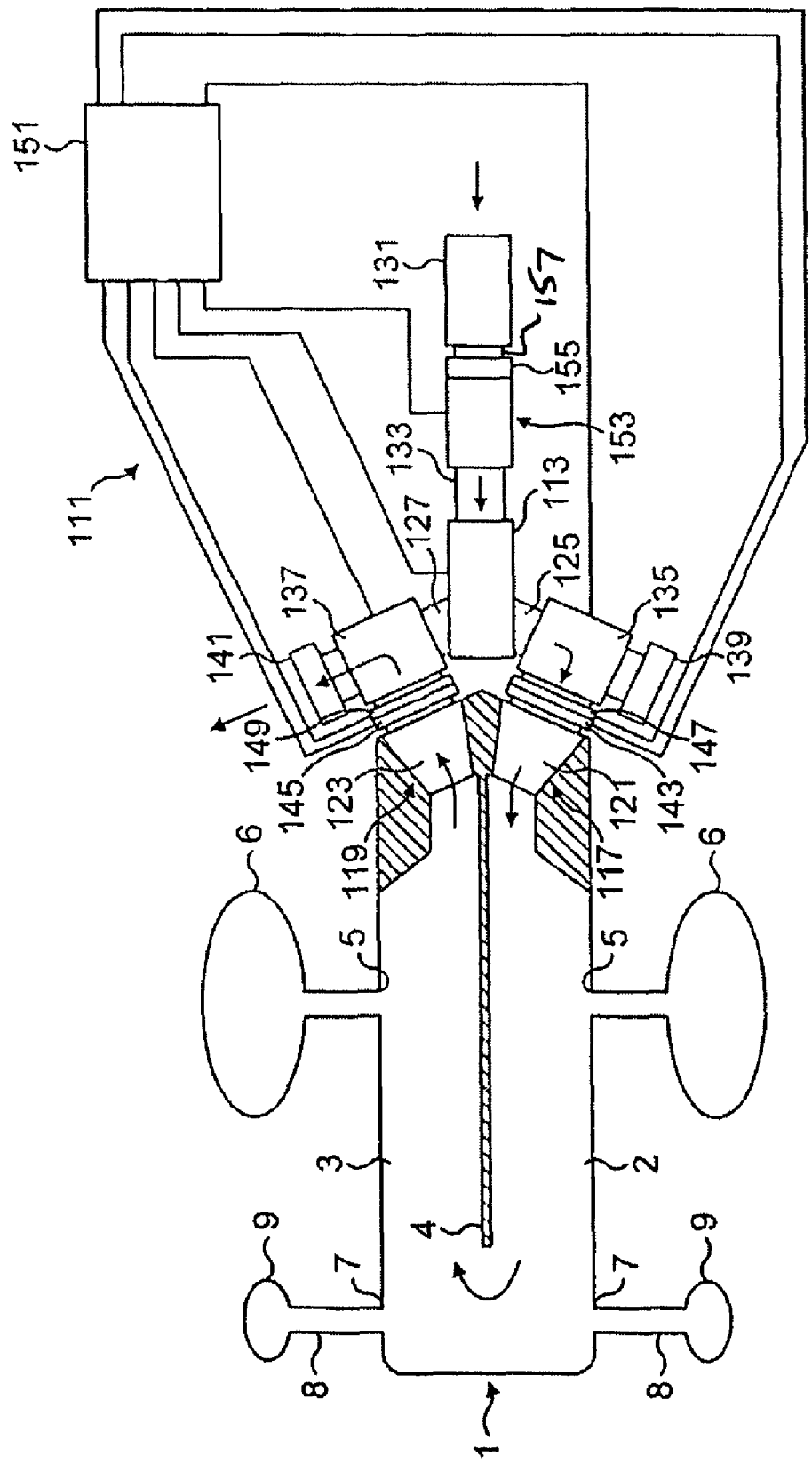
Figure 5C:
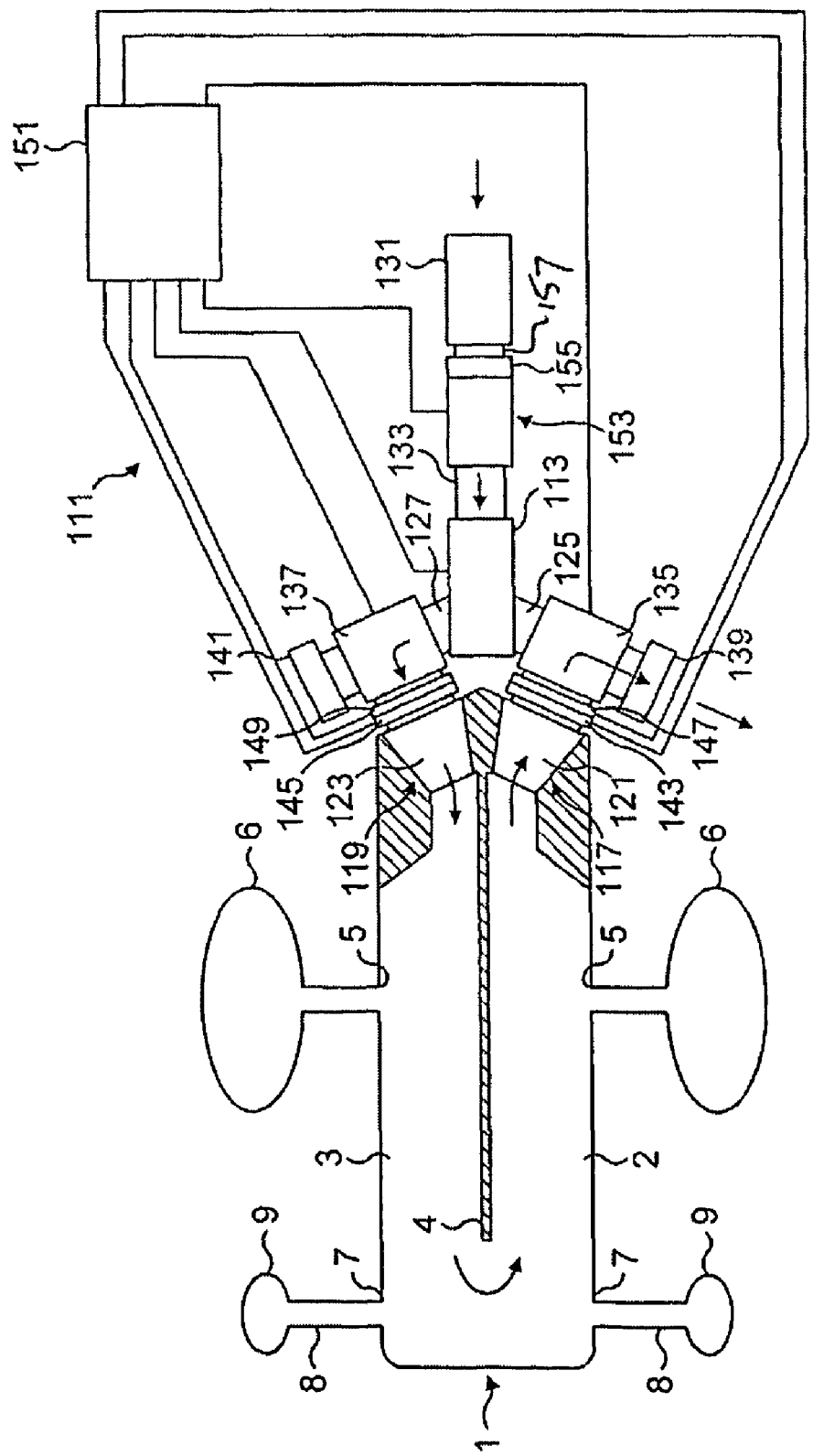

FIG. 3(a) schematically illustrates a nasal delivery device in accordance with a second embodiment of the present invention;

FIG. 3(b) illustrates the nasal delivery device of FIG. 3(a) in a first, delivery configuration;

FIG. 3(c) illustrates the nasal delivery device of FIG. 3(a) in a second, delivery configuration;

FIG. 4(a) schematically illustrates a nasal delivery device in accordance with a third embodiment of the present invention;

FIG. 4(b) illustrates the nasal delivery device of FIG. 4(a) in a first, delivery configuration;

FIG. 4(c) illustrates the nasal delivery device of FIG. 4(a) in a second, delivery configuration;

FIG. 5(a) schematically illustrates a nasal delivery device in accordance with a fourth embodiment of the present invention;

FIG. 5(b) illustrates the nasal delivery device of FIG. 5(a) in a first, delivery configuration; and FIG. 5(c) illustrates the nasal delivery device of FIG. 5(a) in a second, delivery configuration.

Figure 1:
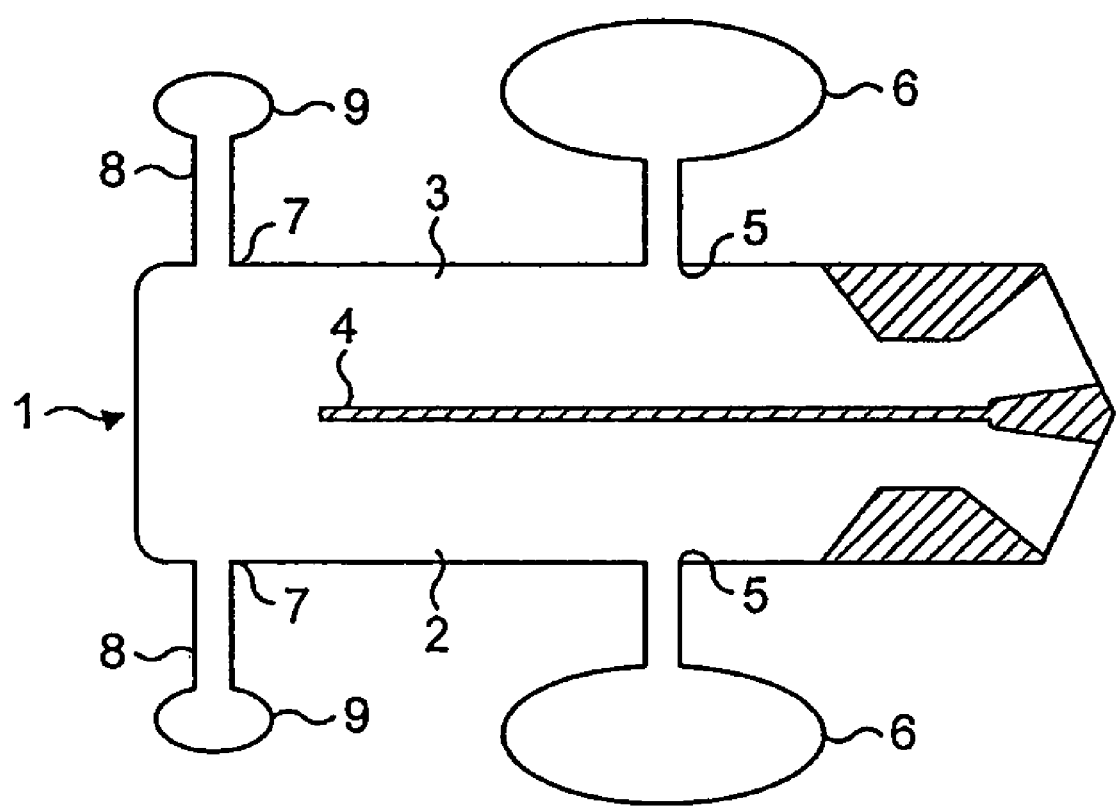
Figure 2A:
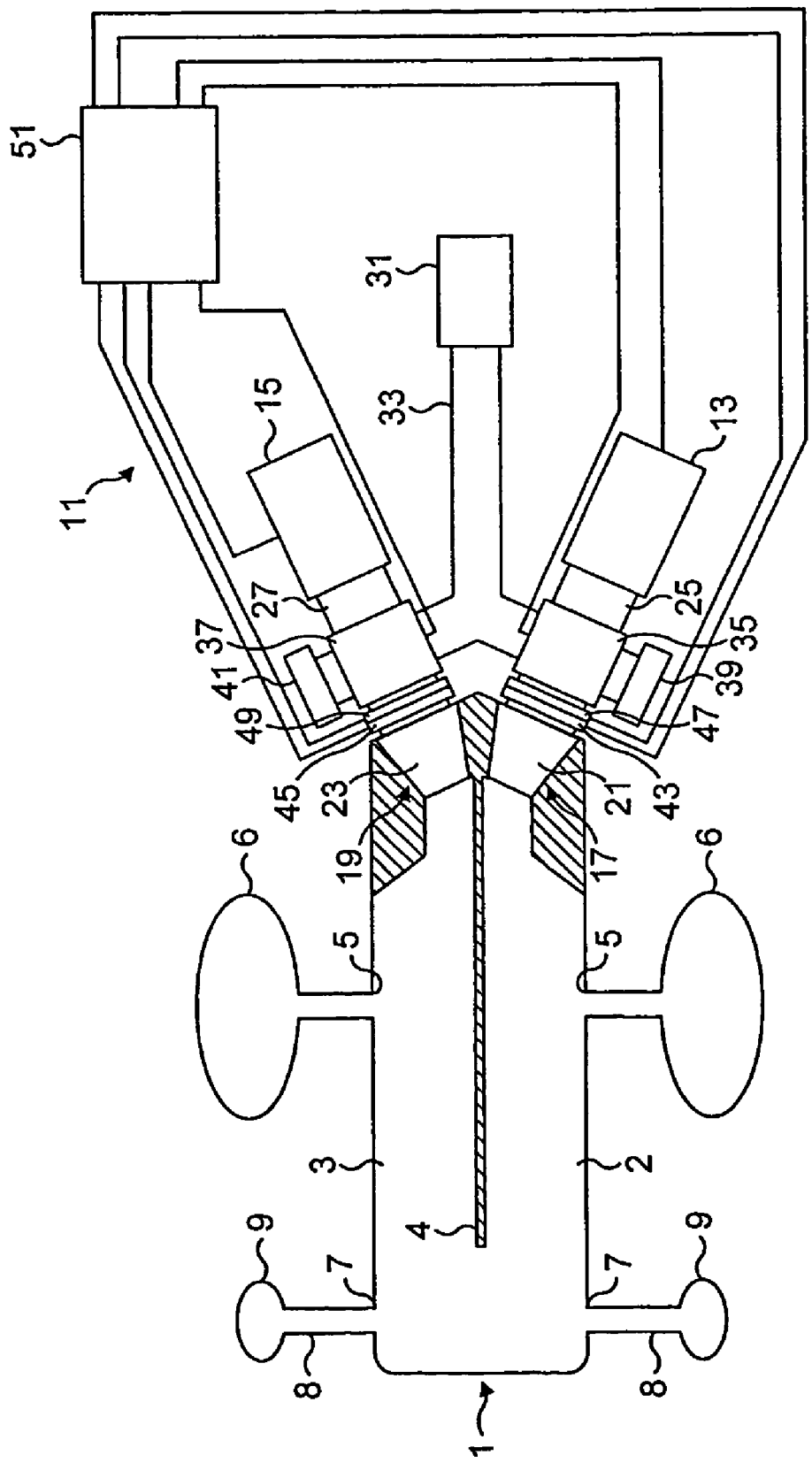
FIG. 2(b) illustrates the nasal delivery device of FIG. 2(a) in a first, delivery configuration.
FIG. 2(c) illustrates the nasal delivery device of FIG. 2(a) in a second, delivery configuration.
Figure 2B:
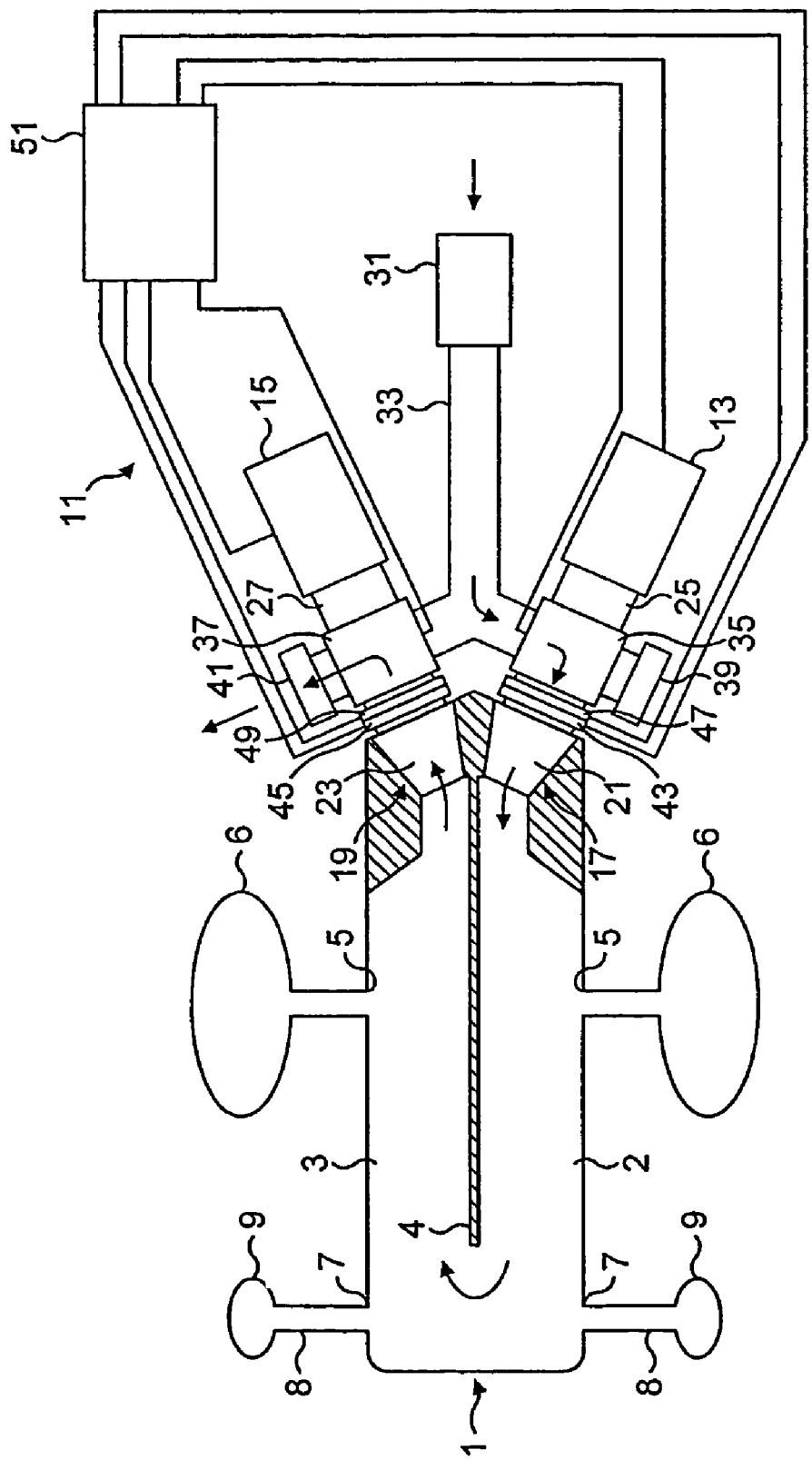
Figure 2C:
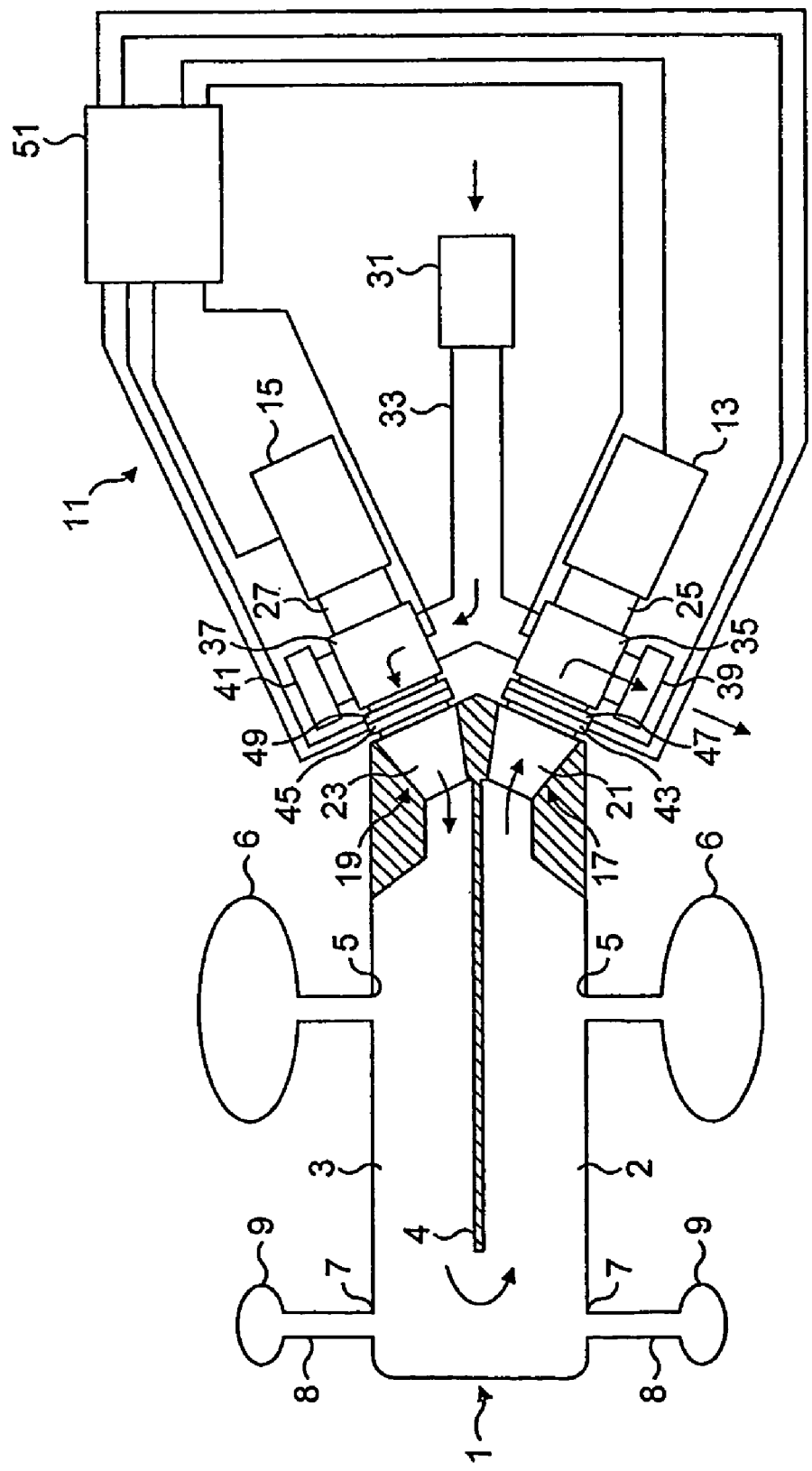

FIGS. 2(a) to (c) illustrate a nasal delivery device 11 in accordance with a first embodiment of the present invention.

The delivery device 11 comprises first and second substance supply units 13, 15 for supplying metered doses of substance. In preferred embodiments the substance comprises a medicament, especially systemic or topical pharmaceuticals, or a vaccine.

In this embodiment the substance supply units 13, 15 comprise aerosol canisters for delivering metered volumes of a propellant, preferably a hydrofluoroalkane (HFA) propellant or the like, containing substance, either as a suspension or solution.

Each of the substance supply units 13, 15 is primeable, in this embodiment by loading a biasing element, and includes a release mechanism, in this embodiment electrically-operated, which, when triggered, releases the biasing element and actuates the respective substance supply unit 13, 15 to deliver a metered dose of substance.

In an alternative embodiment the substance supply units 13, 15 could comprise mechanical delivery pumps, in particular liquid delivery pumps or powder delivery pumps, which deliver metered doses of substance on actuation thereof.

In another alternative embodiment the substance supply units 13, 15 could comprise dry powder delivery units which deliver metered doses of substance, as a dry powder, on actuation thereof.

In yet another alternative embodiment the substance supply units 13, 15 could comprise nebulizers which deliver metered doses of substance, as an aerosol spray, on actuation thereof.

The delivery device 11 further comprises first and second nosepiece units 17, 19 for fitting to respective ones of the nostrils of a subject which are fluidly connected to respective ones of the first and second substance supply units 13, 15. In this embodiment the nosepiece units 17, 19 each comprise a nosepiece 21, 23 for fitting to respective ones of the nostrils of a subject and a flow channel 25, 27 which fluidly connects the respective ones of the nosepieces 21, 23 and the substance supply units 13, 15. In this embodiment the nosepieces 21, 23 are replaceable elements.

The delivery device 11 further comprises a mouthpiece 31 which is gripped by the lips of a subject and through which the subject exhales. In this embodiment the mouthpiece 31 is a replaceable element. In a preferred embodiment the nosepieces 21, 23 and the mouthpiece 31 are integrally formed as a single element such as to allow for replacement after use. In this way, the delivery device 11 can be used to deliver substance to many different subjects and yet avoid cross-contamination from subject to subject.

The delivery device 11 further comprises a gas supply channel 33 which is fluidly connected to the mouthpiece 31.

The delivery device 11 further comprises a valve unit which comprises first and second valves 35, 37 which are disposed in respective ones of the flow channels 25, 27 of the first and second nosepiece units 17, 19 and fluidly connected to the gas supply channel 33 such as to provide for the selective communication of one of the nosepieces 21, 23 with the mouthpiece 31 and the respective one of the substance supply units 13, 15, and the venting of the other of the nosepieces 21, 23 to atmosphere. In this embodiment the valves 35, 37 are electrically-operated valves.

Each of the valves 35, 37 comprises a first port which is fluidly connected to the respective nosepiece 21, 23, a second port which is fluidly connected to the respective substance supply unit 13, 15, a third port which is fluidly connected to the gas supply channel 33, and a fourth port which vents to atmosphere. Each of the valves 35, 37 is operable between a first, delivery position in which the first, second and third ports thereof are open and the fourth port thereof is closed, whereby substance can be delivered by the respective substance supply unit 13, 15 and entrained by the exhalation breath of a subject, and a second, venting position in which the first, second and fourth ports thereof are open and the third port thereof is closed, whereby the exhalation breath of a subject which has been driven through the nasal airway 1 of the subject is vented to atmosphere.

The delivery device 11 further comprises first and second flow resistor units 39, 41 for providing a flow resistance to vented air flow which are fluidly connected to respective ones of the fourth ports of the valves 35, 37. In one embodiment the flow resistor units 39, 41 can each include a filter for preventing the escape of substance.

In this embodiment the flow resistor units 39, 41 each include a flow resistor of fixed flow resistance for providing a fixed flow resistance to vented air flow.

In another embodiment the flow resistor units 39, 41 could include a progressive flow resistor for providing a progressively increasing flow resistance to vented air flow. In one embodiment the flow resistor units 39, 41 could include an inflatable balloon. In one embodiment the flow resistor units 39, 41 could be configured to vent to atmosphere subsequent to the generation of a predetermined pressure, for example, a pressure which exceeds the opening pressure for the paranasal sinus ostia 5 and the tubal ostia 7. With this configuration, following the development of a pressure exceeding the opening pressure for the paranasal sinus ostia 5 and the tubal ostia 7, the flow resistance gradually decreases and the air flow increases. This pressure and flow regime can promote the deposition of airborne particles in the nasal airway 1. Furthermore, this pressure and flow regime ensures that airborne particles are flushed out of the nasal airway 1 before the procedure is terminated, thereby preventing airborne particles, which could subsequently be inhaled, from remaining in the nasal airway 1.

The delivery device 11 further comprises first and second flow meters 43, 45 which are disposed in respective ones of the flow channels 25, 27 of the first and second nosepiece units 17, 19 for detecting the flow rate of the flow therethrough. In this embodiment the flow meters 43, 45 are disposed in the respective ones of the flow channels 25, 27 of the nosepiece units 17, 19 intermediate the respective nosepiece 21, 23 and the respective valve 35, 37.

The delivery device 11 further comprises first and second pressure sensors 47, 49 which are disposed in respective ones of the flow channels 25, 27 of the first and second nosepiece units 17, 19 for detecting the pressure therein. In this embodiment the pressure sensors 47, 49 are disposed in the respective ones of the flow channels 25, 27 of the nosepiece units 17, 19 intermediate the respective nosepiece 21, 23 and the respective valve 35, 37.

The delivery device 11 further comprises a control unit 51 for controlling the operation thereof. The control unit 51 is operably connected to the first and second substance supply units 13, 15, the first and second valves 35, 37 of the valve unit, the first and second flow meters 43, 45, and the first and second pressure sensors 47, 49, whereby the first and second substance supply units 13, 15 can be actuated in response to one or both of detected pressures and flow rates.

Operation of the delivery device 11 will now be described hereinbelow.

Firstly, as illustrated in FIG. 2(a), the nosepieces 21, 23 of the nosepiece units 17, 19 are fitted to the respective nostrils of a subject and the mouthpiece 31 is gripped in the lips of the subject. With this configuration, the delivery device 11 provides for three-point fixation, and thereby ensures reliable repeated delivery to the nasal cavities 2, 3 of a subject.

When first taking the delivery device 11, one of the valves 35, 37 of the valve unit, in this embodiment the first valve 35, is in the delivery position such that the gas supply channel 33 and the respective substance supply unit 13 are in fluid communication with the respective nosepiece 21, and the other of the valves 35, 37 of the valve unit, in this embodiment the second valve 37, is in the venting position such as to vent the other nosepiece 23.

As illustrated in FIG. 2(b), the subject then begins to exhale through the mouthpiece 31, which exhalation acts to close the oropharyngeal velum of the subject and increase the pressure in the nasal airway 1 by the introduction of exhaled air from the exhalation breath thereinto, with the second flow resistor unit 41 providing a flow resistance to the exhaled air flow.

In one mode of operation, the delivery device 11 is configured to be actuated on the generation of a predetermined actuation pressure. In one embodiment the first pressure sensor 43 is utilized to detect the actuation pressure. In another embodiment the second pressure sensor 45 is utilized to detect the actuation pressure. On detection of the actuation pressure, the control unit 51 acts to actuate the first substance supply unit 13 to supply a metered dose of substance, which substance is entrained by the exhalation breath of the subject.

In another mode of operation, the delivery device 11 is configured to be actuated on the generation of a predetermined flow rate. In one embodiment the first flow meter 47 is utilized to detect the actuation flow rate. In another embodiment the second flow meter 49 is utilized to detect the actuation flow rate. On detection of the actuation flow rate, the control unit 51 acts to actuate the first substance supply unit 13 to deliver a metered dose of substance, which substance is entrained by the exhalation breath of the subject.

Following actuation of the first substance supply unit 13, as illustrated in FIG. 2(c), the valve unit is then re-configured by the control unit 51 such that the first valve 35 is moved to the venting position to vent the nosepiece 21 of the first nosepiece unit 17, and the second valve 37 is moved to the delivery position such that the gas supply channel 33 and the second substance supply unit 15 are in fluid communication with the nosepiece 23 of the second nosepiece unit 19.

In one mode of operation, the valve unit is re-configured on detection of a predetermined re-configuration pressure. In one embodiment the first pressure sensor 43 is utilized to detect the re-configuration pressure. In another embodiment the second pressure sensor 45 is utilized to detect the re-configuration pressure. On detection of the re-configuration pressure, the control unit 51 acts to actuate the second substance supply unit 15 to supply a metered dose of substance, which substance is entrained by the exhalation breath of the subject.

In another mode of operation, the delivery device 11 is configured to be actuated on the detection of a predetermined reconfiguration flow volume. In one embodiment the first flow meter 47 is utilized to detect the re-configuration flow volume. In another embodiment the second flow meter 49 is utilized to detect the re-configuration flow volume. On detection of the re-configuration flow volume, the control unit 51 acts to actuate the second substance supply unit 15 to deliver a metered dose of substance, which substance is entrained by the exhalation breath of the subject.

In a further mode of operation, the delivery device 11 is configured to be actuated on the elapse of a predetermined period of time following the actuation of the first substance supply unit 13. On the elapse of the predetermined period of time, the control unit 51 acts to actuate the second substance supply unit 15 to deliver a metered dose of substance, which substance is entrained by the exhalation breath of the subject.

Following actuation of the second substance supply unit 15, the valve unit is then re-configured to the original configuration by the control unit 51 such that the first valve 35 is moved to the delivery position in which the gas supply channel 33 and the first substance supply unit 13 are in fluid communication with the nosepiece 21 of the first nosepiece unit 17, and the second valve 37 is moved to the venting position such as to vent the nosepiece 23 of the second nosepiece unit 19.

In one mode of operation, the valve unit is re-configured on detection of a predetermined re-configuration pressure. In one embodiment the first pressure sensor 43 is utilized to detect the re-configuration pressure. In another embodiment the second pressure sensor 45 is utilized to detect the re-configuration pressure.

In another mode of operation, the valve unit is re-configured on detection of a predetermined re-configuration flow volume. In one embodiment the first flow meter 47 is utilized to detect the reconfiguration flow volume. In another embodiment the second flow meter 49 is utilized to detect the re-configuration flow volume.

In a further mode of operation, the valve unit is re-configured on the elapse of a predetermined period of time following the actuation of the second substance supply unit 15.

In this way, the delivery device 11 provides for the successive delivery of substance through each of the nostrils of the subject, which delivery is advantageous, both in terms of compliance and, particularly, in delivering substance to targeted posterior regions of the nasal airway 1.

In another embodiment the delivery device 11 could be configured such that the valve unit is re-configured more than twice in each operation, such as to provide for the repeated delivery of substance to alternate ones of the nostrils of the subject in each operation of the delivery device 11.

FIGS. 3(*a*) to (*c*) illustrate a nasal delivery device 11 in accordance with a second embodiment of the present invention.

The delivery device 11 of this embodiment is very similar to the delivery device 11 of the above-described first embodiment, and thus, in order to avoid unnecessary duplication of description, only the differences will be described in detail, with like reference signs designating like parts.

The delivery device 11 of this embodiment differs from that of the above-described first embodiment in further comprising an exhalation breath actuatable gas supply unit 53 which is fluidly connected to the gas supply channel 33 for delivering a gas flow thereto and operably connected to the control unit 51, and in that the mouthpiece 31 is in fluid communication with the gas supply unit 53 and not the gas supply channel 33, whereby a gas flow is delivered by the gas supply unit 53 in response to exhalation by a subject into the mouthpiece 31.

The gas supply unit 53 includes a trigger mechanism 55 for actuating the same in response to exhalation by the subject, with the trigger mechanism 55 being operably coupled to the mouthpiece 31 such as to be actuated by the exhalation breath of the subject. In this embodiment the trigger mechanism 55 comprises a pressure sensor for actuating the gas supply unit 53 in response to the detection of a predetermined actuation pressure. In another embodiment the trigger mechanism 55 could comprise a flow meter for actuating the gas supply unit 53 in response to the detection of a predetermined flow rate.

In this embodiment the mouthpiece 31 includes a diaphragm 57 which is acted upon by the exhalation breath of the subject to actuate the trigger mechanism 55 on the generation of the predetermined actuation pressure. With this configuration, where the mouthpiece 31 is disposable, no part of the delivery device 11, other than the disposable mouthpiece 31, is exposed to the exhalation breath of the subject, and the delivery device 11 can be used to deliver substance to many subjects, such as in mass immunization or mass vaccination, without the risk of cross-contamination.

Operation of the delivery device 11 is the same as for the above-described first embodiment, with a gas flow being provided by the gas supply unit 53 instead of being developed by the exhalation breath of the subject.

In one embodiment the gas supply unit 53 is configured to deliver a gas flow at such a flow rate as to develop a predetermined pressure in the nasal airway 1.

In another embodiment the gas supply unit 53 could be configured to deliver a gas flow which has an alternating flow and is such as to develop an alternating pressure within the nasal airway 1. By cycling the pressure within the nasal airway 1, improved delivery of substance to the paranasal sinuses 6 and the tuba auditiva 8 and the middle ears 9 can be achieved. In one embodiment the delivery device 11 can be configured to provide for delivery of substance through only one nostril of the subject.

In a further embodiment, at least one of the first and second flow resistors 39, 41 could comprise an expandable chamber, such as an inflatable balloon, and the gas supply unit 53 could be configured alternately to deliver and withdraw a volume of gas through the nasal airway 1 from either one or alternately both of the nostrils of the subject, which delivery and withdrawal would be such as to cause a volume of gas which entrains substance to be flushed repeatedly through the nasal airway 1 in opposite directions. Repeatedly flushing a volume of gas entraining substance in alternate directions through the nasal airway 1 would provide for improved delivery of substance. In one embodiment the delivery device 11 can be configured to provide for delivery of substance through only one nostril of the subject.

FIGS. 4(*a*) to (*c*) illustrate a nasal delivery device 111 in accordance with a third embodiment of the present invention.

The delivery device 111 comprises a substance supply unit 113 for supplying a metered dose of substance. In preferred embodiments the substance comprises a medicament, especially systemic or topical pharmaceuticals, or a vaccine.

In this embodiment the substance supply unit 113 comprises a nebulizer which delivers a metered dose of substance, here continuously as an aerosol spray, on actuation thereof.

The delivery device 111 further comprises first and second nosepiece units 117, 119 for fitting to respective ones of the nostrils of a subject. In this embodiment the nosepiece units 117, 119 each comprise a nosepiece 121, 123 for fitting to respective ones of the nostrils of a subject and a flow channel 125, 127 which fluidly connects the respective one of the nosepieces 121, 123 to the substance supply unit 113. In this embodiment the nosepieces 121, 123 are replaceable elements.

The delivery device 111 further comprises a mouthpiece 131 which is gripped by the lips of a subject and through which the subject exhales. In this embodiment the mouthpiece 131 is a replaceable element. In a preferred embodiment the nosepieces 121, 123 and the mouthpiece 131 are integrally formed as a single element such as to allow for replacement after use. In this way, the delivery device 111 can be used with many different subjects, for example, in mass immunization or mass vaccination, and yet avoid the possibility of cross-contamination from subject to subject.

The delivery device 111 further comprises a gas supply channel 133 which fluidly connects the substance supply unit 113 and the mouthpiece 131.

The delivery device 111 further comprises a valve unit which comprises first and second valves 135, 137 which are disposed in respective ones of the flow channels 125, 127 of the first and second nosepiece units 117, 119 such as to provide for the selective communication of one of the nosepieces 121, 123 with the substance supply unit 113 and mouthpiece 131, and the venting of the other of the nosepieces 121, 123 to atmosphere. In this embodiment the valves 135, 137 are electrically-operated valves.

Each of the valves 135, 137 comprises a first port which is fluidly connected to the respective nosepiece 121, 123, a second port which is fluidly connected to the substance supply unit 113, and a third port which vents to atmosphere. Each of the valves 135, 137 is operable between a first, delivery position in which the first and second ports thereof are open and the third port thereof is closed, whereby substance can be delivered by the substance supply unit 113 and entrained by the exhalation breath of a subject, and a second, venting position in which the first and third ports thereof are open and the second port thereof is closed, whereby the exhalation breath of a subject which has been driven through the nasal airway 1 of the subject is vented to atmosphere.

The delivery device 111 further comprises first and second flow resistor units 139, 141 for providing a flow resistance to vented air flow which are fluidly connected to respective ones of the third ports of the valves 135, 137. In one embodiment the flow resistor units 139, 141 can each include a filter for preventing the escape of substance.

In this embodiment the flow resistor units 139, 141 each include a flow resistor of fixed flow resistance for providing a fixed flow resistance to vented air flow.

In another embodiment the flow resistor units 139, 141 could include a progressive flow resistor for providing a progressively increasing flow resistance to vented air flow. In one embodiment the flow resistor units 139, 141 could include an inflatable balloon. In one embodiment the flow resistor units 139, 141 could be configured to vent to atmosphere subsequent to the generation of a predetermined pressure, for example, a pressure which exceeds the opening pressure for the paranasal sinus ostia 5 and the tubal ostia 7. With this configuration, following the development of a pressure exceeding the opening pressure for the paranasal sinus ostia 5 and the tubal ostia 7, the flow resistance gradually decreases and the air flow increases. This pressure and flow regime can promote the deposition of airborne particles in the nasal airway 1. Furthermore, this pressure and flow regime ensures that airborne particles are flushed out of the nasal airway 1 before the procedure is terminated, thereby preventing airborne particles, which could subsequently be inhaled, from remaining in the nasal airway 1.

The delivery device 111 further comprises first and second flow meters 143, 145 which are disposed in respective ones of the flow channels 125, 127 of the first and second nosepiece units 117, 119 for detecting the flow rate of the flow therethrough. In this embodiment the flow meters 143, 145 are disposed in the respective ones of the flow channels 125, 127 of the nosepiece units 117, 119 intermediate the respective nosepiece 121, 123 and the respective valve 135, 137.

The delivery device 111 further comprises first and second pressure sensors 147, 149 which are disposed in respective ones of the flow channels 125, 127 of the first and second nosepiece units 117, 119 for detecting the pressure therein. In this embodiment the pressure sensors 147, 149 are disposed in the respective ones of the flow channels 125, 127 of the nosepiece units 117, 119 intermediate the respective nosepiece 121, 123 and the respective valve 135, 137.

The delivery device 111 further comprises a control unit 151 for controlling the operation thereof. The control unit 151 is operably connected to the substance supply unit 113, the first and second valves 135, 137 of the valve unit, the first and second flow meters 143, 145, and the first and second pressure sensors 147, 149, whereby the substance supply unit 113 can be actuated in response to one or both of detected pressures and flow rates.

Operation of the delivery device 111 will now be described hereinbelow.

Firstly, as illustrated in FIG. 4(a), the nosepieces 121, 123 of the nosepiece units 117, 119 are fitted to the respective nostrils of a subject and the mouthpiece 131 is gripped in the lips of the subject. With this configuration, the delivery device 111 provides for three-point fixation, and thereby ensures reliable repeated delivery to the nasal cavities 2, 3 of a subject.

When first taking the delivery device 111, one of the valves 135, 137 of the valve unit, in this embodiment the first valve 135, is in the delivery position such that the substance supply unit 113 is in fluid communication with the nosepiece 121 of the first nosepiece unit 117, and the other of the valves 135, 137 of the valve unit, in this embodiment the second valve 137, is in the venting position such as to vent the nosepiece 123 of the second nosepiece unit 119.

As illustrated in FIG. 4(b), the subject then begins to exhale through the mouthpiece 131, which exhalation acts to close the oropharyngeal velum of the subject and increase the pressure in the nasal airway 1 by the introduction of exhaled air from the exhalation breath thereinto, with the second flow resistor unit 141 providing a flow resistance to the exhaled air flow.

In one mode of operation, the delivery device 111 is configured to be actuated on the generation of a predetermined actuation pressure. In one embodiment the first pressure sensor 143 is utilized to detect the actuation pressure. In another embodiment the second pressure sensor 145 is utilized to detect the actuation pressure. On detection of the actuation pressure, the control unit 151 acts to actuate the substance supply unit 113 to commence delivery of a metered dose of substance, which substance is entrained by the exhalation breath of the subject.

In another mode of operation, the delivery device 111 is configured to be actuated on the generation of a predetermined flow rate. In one embodiment the first flow meter 147 is utilized to detect the actuation flow rate. In another embodiment the second flow meter 149 is utilized to detect the actuation flow rate. On detection of the actuation flow rate, the control unit 151 acts to actuate the substance supply unit 113 to commence delivery of a metered dose of substance, which substance is entrained by the exhalation breath of the subject.

Following actuation of the substance supply unit 113, the valve unit remains in the one configuration for a predetermined period of time, in this embodiment for half of the time period required for the delivery of a predetermined metered dose of substance by the substance supply unit 113.

Following the elapse of the predetermined period of time, as illustrated in FIG. 4(c), the valve unit is then re-configured by the control unit 151 such that the first valve 135 is moved to the venting position to vent the nosepiece 121 of the first nosepiece unit 117, and the second valve 137 is moved to the delivery position such that the substance supply unit 113 is in fluid communication with the nosepiece 123 of the second nosepiece unit 119.

In this way, the delivery device 111 provides for the successive delivery of substance through each of the nostrils of the subject, which delivery is advantageous, both in terms of compliance and, particularly, in delivering substance to targeted posterior regions of the nasal airway 1.

In another embodiment the delivery device 111 could be configured such that the valve unit is re-configured more than twice in each operation, such as to provide for the repeated delivery of substance to alternate ones of the nostrils of the subject in each operation of the delivery device 111. In this embodiment this repeated alternation of the delivery nostril is achieved by directing the exhalation breath of a subject to alternate ones of the nostrils of the subject.

In alternative embodiments the substance supply unit 113 could comprise an aerosol canister for delivering a metered volume of a propellant, preferably a hydrofluoroalkane (HFA) propellant or the like, containing substance, either as a suspension or solution, a mechanical delivery pump, in particular a liquid delivery pump or a powder delivery pump, which delivers a metered dose of substance on actuation thereof, or a dry powder delivery unit which delivers a metered dose of substance, as a dry powder, on actuation thereof. These substance supply units 113 are primed, in one embodiment by loading a biasing element, and include a release mechanism, in this embodiment electrically-operated, which, when triggered, releases the biasing element and actuates the substance supply unit 113 to deliver a metered dose of substance. In such embodiments the substance supply unit 113 can be actuated for each alternation of the valve unit.

FIGS. 5(*a*) to (*c*) illustrate a nasal delivery device 111 in accordance with a fourth embodiment of the present invention.

The delivery device 111 of this embodiment is very similar to the delivery device 111 of the above-described third embodiment, and thus, in order to avoid unnecessary duplication of description, only the differences will be described in detail, with like reference signs designating like parts The delivery device 111 of this embodiment differs from that of the above-described third embodiment in further comprising an exhalation breath actuatable gas supply unit 153 which is fluidly connected to the gas supply channel 133 for delivering a gas flow thereto and operably connected to the control unit 151, and in that the mouthpiece 131 is in fluid communication with the gas supply unit 153 and not the gas supply channel 133, whereby a gas flow is delivered by the gas supply unit 153 in response to exhalation through the mouthpiece 131.

The gas supply unit 153 includes a trigger mechanism 155 for actuating the same in response to exhalation by the subject, with the trigger mechanism 155 being operably coupled to the mouthpiece 131 such as to be actuated by the exhalation breath of the subject. In this embodiment the trigger mechanism 155 comprises a pressure sensor for actuating the gas supply unit 153 in response to the detection of a predetermined actuation pressure. In another embodiment the trigger mechanism 155 could comprise a flow meter for actuating the gas supply unit 153 in response to the detection of a predetermined flow rate.

In this embodiment the mouthpiece 131 includes a diaphragm 157 which is acted upon by the exhalation breath of the subject to actuate the trigger mechanism 155 on the generation of the predetermined actuation pressure. With this configuration, where the mouthpiece 131 is disposable, no part of the delivery device 111, other than the disposable mouthpiece 131, is exposed to the exhalation breath of the subject, and the delivery device 111 can be used to deliver substance to many subjects, such as in mass immunization or mass vaccination, without the risk of cross-contamination.

Operation of the delivery device 111 is the same as for the above-described third embodiment, with a gas flow being provided by the gas supply unit 153 instead of being developed by the exhalation breath of the subject.

In one embodiment the gas supply unit 153 is configured to deliver a gas flow at such a flow rate as to develop a predetermined pressure in the nasal airway 1.

In another embodiment the gas supply unit 153 could be configured to deliver a gas flow which has an alternating flow and is such as to develop an alternating pressure within the nasal airway 1. By cycling the pressure within the nasal airway 1, improved delivery of substance to the paranasal sinuses 6 and the tuba auditiva 8 and the middle ears 9 can be achieved. In one embodiment the delivery device 111 can be configured to provide for delivery of substance through only one nostril of the subject.

In a further embodiment, at least one of the first and second flow resistors 139, 141 could comprise an expandable chamber, such as an inflatable balloon, and the gas supply unit 153 could be configured alternately to deliver and withdraw a volume of gas through the nasal airway 1 from either one or alternately both of the nostrils of the subject, which delivery and withdrawal would be such as to cause a volume of gas which entrains substance to be flushed repeatedly through the nasal airway 1 in opposite directions. Repeatedly flushing a volume of gas entraining substance in alternate directions through the nasal airway 1 would provide for improved delivery of substance. In one embodiment the delivery device 111 can be configured to provide for delivery of substance through only one nostril of the subject.

Finally, it will be understood that the present invention has been described in its preferred embodiments and can be modified in many different ways without departing from the scope of the invention as defined by the appended claims.

In the described embodiments the mouthpieces 31, 131 are configured to be gripped in the lips of a subject. In alternative embodiments the mouthpieces 31, 131 could be configured to be gripped by the teeth of a subject and sealed by the lips of the subject. In preferred embodiments the mouthpieces 31, 131 could be specifically configured to have one or both of a shape or geometry which allows the delivery devices to be gripped repeatedly in the same position, thereby providing for the respective nosepieces 21, 23, 121, 123 to be reliably inserted in the same position in the nasal cavities 2, 3.

In preferred embodiments the delivery devices 11, 111 are configured to deliver substance through one nostril of a subject at such a pressure as to flow around the posterior margin of the nasal septum 4 and out of the other nostril of the subject, thereby achieving bi-directional delivery through the nasal cavities 2, 3 as disclosed in WO-A-00/51672. In alternative embodiments the delivery devices 11, 111 can be configured to deliver substance at a reduced pressure which is not sufficient to achieve bi-directional delivery through the nasal cavities 2, 3.

The invention claimed is:

1. A nasal delivery device for delivering substance to a nasal airway of a subject, comprising:
   first and second nosepiece units, each including a nosepiece for fitting to respective nostrils of a subject;
   at least one substance supply unit for supplying a metered dose of substance for delivery to the nasal airway of the subject;
   a valve unit for selectively fluidly connecting the at least one substance supply unit alternately to respective ones of the nosepiece units, the valve unit configured to alternately (i) establish communication between the at least one substance supply unit and the first nosepiece unit and (ii) establish communication between the at least one substance supply unit and the second nosepiece unit; and
   a mouthpiece through which the subject in use exhales to cause closure of the oropharyngeal velum of the subject during delivery of substance.

2. The delivery device of claim 1, further comprising:
   a gas supply channel for supplying a gas flow for entraining substance supplied by the at least one substance supply unit.

3. The delivery device of claim 2, wherein the mouthpiece is fluidly connected to the gas supply channel, whereby the gas flow is an air flow developed by an exhalation breath of the subject.

4. The delivery device of claim 2, further comprising:
   a gas supply unit which is fluidly connected to the gas supply channel for delivering a gas flow through the gas supply channel.

5. The delivery device of claim 4, wherein the gas supply unit is an exhalation breath actuatable unit which is fluidly connected to the mouthpiece such as to be actuated on exhalation by the subject.

6. The delivery device of claim 2, wherein the device is configured to deliver the gas flow at a driving pressure which is such as to cause the gas flow to flow around the posterior margin of the nasal septum and through the nasal airway and wherein the valve unit is configured alternatively (i) to vent the nasal airway of the subject through the second nosepiece unit when the at least one substance supply unit is in communication with the first nosepiece and (ii) to vent the nasal airway of the subject through the first nosepiece unit when the at least one substance supply unit is in communication with the second nosepiece.

7. The nasal delivery device of claim 6, wherein the device is configured such that the venting occurs through the respective nosepiece unit to the atmosphere.

8. The delivery device of claim 1, further comprising:
at least one flow resistor to which a nosepiece unit is vented.

9. The delivery device of claim 8, wherein the flow resistor has a fixed flow resistance for providing a fixed flow resistance to the gas flow.

10. The delivery device of claim 8, wherein the flow resistor is a progressive resistor for progressively providing an increasing flow resistance to the gas flow.

11. The delivery device of claim 10, wherein the progressive resistor comprises an expandable member which provides a progressively increasing resistance to the gas flow.

12. The delivery device of claim 1, further comprising:
a control unit for controlling the valve unit such as to provide for alternate delivery of substance through respective ones of the first and second nosepiece units.

13. The delivery device of claim 1, comprising:
a single substance supply unit for supplying substance for delivery alternately to respective ones of the first and second nosepiece units.

14. The delivery device of claim 1, comprising:
first and second substance supply units for supplying substance for delivery to respective ones of the first and second nosepiece units.

15. The delivery device of claim 1, wherein the valve unit comprises first and second valves, each being fluidly connected to a respective one of the first and second nosepiece units.

16. A method of delivering substance to a nasal airway of a subject, comprising the steps of:
taking the device of claim 1;
fitting the first and second nosepiece units to respective nostrils of a subject;
delivering a metered dose of substance alternately through respective ones of the nosepiece units using the at least one substance supply unit and the valve unit; and
exhaling through the mouthpiece during delivery of substance to cause closure of the oropharyngeal velum of the subject.

17. The method of claim 16, wherein substance is delivered in a gas flow.

18. The method of claim 17, wherein the gas flow is an air flow developed by an exhalation breath of the subject.

19. The method of claim 17, wherein the gas flow is a gas flow separate to an exhalation breath of the subject.

20. The method of claim 17, wherein substance is delivered alternately to one of the nosepiece units and the other of the nosepiece units is vented, such that, where the gas flow is at a driving pressure which is such as to cause the gas flow to flow around the posterior margin of the nasal septum and through the nasal airway, the gas flow delivered to the one nosepiece unit is vented through the other nosepiece unit.

21. The method of claim 20, wherein the gas flow is vented through a flow resistor.

22. The method of claim 21, wherein the flow resistor has a fixed flow resistance and provides a fixed flow resistance to the gas flow.

23. The method of claim 21, wherein the flow resistor is a progressive resistor which provides a progressively increasing flow resistance to the gas flow.

24. The method of claim 23, wherein the progressive resistor comprises an expandable member which provides a progressively increasing resistance to the gas flow.

25. The method of claim 20, wherein the device is configured such that the venting occurs through the respective nosepiece unit to the atmosphere.

26. The method of claim 16, wherein substance is supplied from a single substance supply unit.

27. The method of claim 16, wherein substance is supplied to the first and second nosepiece units from respective ones of first and second substance supply units.

28. A nasal delivery device for delivering substance to a nasal airway of a subject, comprising:
a mouthpiece configured to receive an exhalation breath from the subject to cause closure of the oropharyngeal velum of the subject;
at least one delivery unit for delivering a metered dose of substance to a nasal airway of the subject on exhalation by the subject; and
an exogenous gas supply unit for supplying a gas flow into the nasal airway of the subject and configured to provide an alternating pressure in the nasal airway of the subject during the exhalation breath.

29. The delivery device of claim 28, wherein the exogenous gas supply unit is an exhalation breath actuatable unit which is fluidly connected to the mouthpiece such as to be actuated on exhalation by the subject.

30. A method of delivering substance to a nasal airway of a subject, comprising the steps of:
taking the device of claim 28;
delivering a metered dose of substance to a nasal airway of a subject using the at least one delivery unit;
the subject delivering an exhalation breath through the mouthpiece during delivery of the substance by the at least one delivery unit, to cause closure of the oropharyngeal velum of the subject; and
the exogenous gas supply unit supplying an exogenous gas flow having an alternating pressure into the nasal airway of the subject during the exhalation breath.

31. The nasal delivery device of claim 28, further comprising a valve unit configured to alternately (i) establish communication between the exogenous gas supply unit and a first nostril of the subject and (ii) establishing communication between the exogenous gas supply unit and the second nostril.

32. A method of delivering substance to a nasal airway of a subject, comprising the steps of:
taking the device of claim 31;
delivering a metered dose of substance to a nasal airway of a subject using the at least one delivery unit;
the subject delivering an exhalation breath through the mouthpiece during delivery of the substance by the at least one delivery unit, to cause closure of the oropharyngeal velum of the subject; and
supplying an exogenous gas flow having an alternating pressure into the nasal airway of the subject during the exhalation breath using the exogenous gas supply unit and the valve unit such that a communication is alternately established between the exogenous gas supply unit and (i) a first nostril of the subject and (ii) a second nostril of the subject.

33. A nasal delivery device for delivering substance to a nasal airway of a subject, comprising:
   a mouthpiece configured to receive an exhalation breath from the subject to cause closure of the oropharyngeal velum of the subject;
   at least one delivery unit for delivering a metered dose of substance to a nasal airway of the subject on exhalation by the subject; and
   an exogenous gas supply unit configured to alternately deliver and withdraw a volume of exogenous gas entraining the substance through the nasal airway of the subject during the exhalation breath, such as to cause the entrained substance to be flushed repeatedly through the nasal airway in alternate directions.

34. A method of delivering substance to a nasal airway of a subject, comprising the steps of:
   taking the device of claim 33;
   delivering a metered dose of substance to a nasal airway of a subject using the at least one delivery unit;
   the subject delivering an exhalation breath through the mouthpiece during delivery of the substance by the at least one delivery unit, to cause closure of the oropharyngeal velum of the subject; and
   the exogenous gas supply unit alternately delivering and withdrawing a volume of exogenous gas entraining the substance through the nasal airway of the subject during the exhalation breath such as to cause the entrained substance to be flushed repeatedly through the nasal airway in alternate directions.

* * * * *